(12) United States Patent
Hauser et al.

(10) Patent No.: US 12,303,522 B2
(45) Date of Patent: May 20, 2025

(54) COMPOSITION COMPRISING HUMAN MILK OLIGOSACCHARIDES FOR USE IN IMPROVING, ENHANCING, PROMOTING OR MODULATING A GABAERGIC FUNCTION IN THE CENTRAL NERVOUS SYSTEM

(71) Applicant: SOCIETE DES PRODUITS NESTLE S.A., Vevey (CH)

(72) Inventors: Jonas Hauser, Lausanne (CH); Jian Yan, Seattle, WA (US)

(73) Assignee: Societe des Produits Nestle S.A., Vevey (CH)

( * ) Notice: Subject to any disclaimer, the term of this patent is extended or adjusted under 35 U.S.C. 154(b) by 765 days.

(21) Appl. No.: 17/255,013

(22) PCT Filed: May 21, 2019

(86) PCT No.: PCT/EP2019/063035
§ 371 (c)(1),
(2) Date: Dec. 22, 2020

(87) PCT Pub. No.: WO2020/001863
PCT Pub. Date: Jan. 2, 2020

(65) Prior Publication Data
US 2021/0268005 A1    Sep. 2, 2021

Related U.S. Application Data

(60) Provisional application No. 62/689,297, filed on Jun. 25, 2018.

(51) Int. Cl.
*A61K 31/702* (2006.01)
*A23K 10/18* (2016.01)
*A23K 20/163* (2016.01)
*A23L 33/00* (2016.01)
*A23L 33/135* (2016.01)

(52) U.S. Cl.
CPC ............ *A61K 31/702* (2013.01); *A23K 10/18* (2016.05); *A23K 20/163* (2016.05); *A23L 33/135* (2016.08); *A23L 33/40* (2016.08)

(58) Field of Classification Search
CPC . A61K 31/702; A23K 20/163; A23V 2002/00
See application file for complete search history.

(56) References Cited

U.S. PATENT DOCUMENTS

| | | | |
|---|---|---|---|
| 2012/0171166 A1* | 7/2012 | Chow | A61K 31/702 424/93.4 |
| 2013/0195803 A1* | 8/2013 | German | A61K 35/745 435/97 |
| 2015/0231213 A1 | 8/2015 | Chichlowski et al. | |
| 2018/0103675 A1 | 4/2018 | Chichlowski et al. | |

FOREIGN PATENT DOCUMENTS

| | | |
|---|---|---|
| CL | 2020003135 A1 | 6/2021 |
| RU | 2473347 C1 | 1/2013 |
| WO | 2012069416 A1 | 5/2012 |
| WO | 2015086789 | 6/2015 |
| WO | 2016066735 | 5/2016 |
| WO | 2016146789 | 9/2016 |
| WO | WO-2016146789 A1 * | 9/2016 ............ A23L 33/10 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Thapar et al., Arch. Dis. Child, 2012, 97, p. 260-265. (Year: 2012).*
Mayo Clinic Staff, Autism spectrum disorder—Symptoms and causes, website dated Jan. 6, 2018, accessed online at https://www.mayoclinic.org on Aug. 22, 2023, 11 pages. (Year: 2018).*
Vazquez et al., PLoS One, 2016, 11(11), article e0166070, 14 pages. (Year: 2016).*
Neeser et al., Journal of Dairy Science, 1991, 74(9), p. 2860-2871. (Year: 1991).*
Robertson et al., Current Biology, 2016, 26, p. 80-85. (Year: 2016).*
Russian Office Action for Appl No. 2021100872/10 dated Nov. 10, 2023.
Yunfei et al., "Principles of General Anesthesia and New Research Advances", 2005, pp. 144-147.
Yizhang, "Synapse", 2014, pp. 155-157.
Office Action Received for Application No. CN201980037220.2, mailed on Dec. 27, 2023, 6 Pages of Official Copy.
Chinese Office Action for Appl No. 201980037220.2 dated Feb. 28, 2023.
Chile Office Action for Appl No. 2020-02978 dated Nov. 4, 2024, 2 pages.

* cited by examiner

Primary Examiner — Jonathan S Lau
(74) Attorney, Agent, or Firm — K&L Gates LLP (57) ABSTRACT

The invention relates to a nutritional composition comprising human milk oligosaccharide (HMO) having an effect on in a mammal to improve, enhance, promote or modulate a GABAergic function in the CNS, preferably in a human infant or a young children between birth and 7 years. The composition can be an infant formula. The HMO may be 2FL, diFL and/or LNT and or LNnT or combinations thereof.

11 Claims, 2 Drawing Sheets

COMPOSITION COMPRISING HUMAN MILK OLIGOSACCHARIDES FOR USE IN IMPROVING, ENHANCING, PROMOTING OR MODULATING A GABAERGIC FUNCTION IN THE CENTRAL NERVOUS SYSTEM

CROSS REFERENCE TO RELATED APPLICATIONS

The present application is a National Stage of International Application No. PCT/EP2019/063035, filed on May 21, 2019, which claims priority to U.S. Provisional Patent Application No. 62/689,297, filed on Jun. 25, 2018, the entire contents of which are being incorporated herein by reference.

BACKGROUND

The present invention generally relates to the field of neuronal health, neuronal protection and neuronal development. Specifically, the invention relates to a composition for use in supporting neurodevelopment, in particular improving, enhancing, promoting or modulating a function pertaining to or affecting the neurotransmitter gamma-amino butyric acid (GABA) in the central nervous system (CNS) and other related cognitive benefits, especially in infants and young children, preferably for the target group of (preterm or term) infants or a young children between birth and 7 years.

More specifically, the invention relates to administration of human milk oligosaccharides (HMO), optionally in combination with further prebiotic oligosaccharides, in particular fructo-oligosaccharides (FOS), or oligofructose (OF) and/or bovine milk oligosaccharides (BMOS) for improving, enhancing, promoting or modulating a GABAergic function in the CNS, in particular filtering of information or the capacity to focus or concentrate on a mental or physical activity.

The CNS, and in particular the brain, drives the cognitive functions. The cerebral cortex, which is a sheet of neural tissue that is outermost to the cerebrum of the mammalian brain, plays a key role in attention, perceptual awareness, higher order cognition (executive function) and information integration of sensory input.

CNS development and maturation is a highly complex biological phenomenon that involves a number of physiological processes including, for example, neuron and glial cell growth and differentiation, neuronal pathfinding and branching, and establishment of inter neuronal communication (nerve signals) via axon growth and synaptogenesis.

Neuronal plasticity, which is defined as the ability of the brain to continuously adapt its functions and structural organization to changing requirements is important in nervous system maturation and adult function. It is essential for the correct functioning of the brain and necessary for cognition, learning and memory. Some of the neuronal markers, including proteins and neurotrophic factors, like Brain Derived Neurotrophic Factor (BDNF) required for, or at least, associated with these physiological processes, have been identified in the literature and studied [Huang, E. J. and Reichardt, L. F. (2001); Neurotrophins: Roles in Neuronal Development and Function, *Annu. Rev. Neurosci.*, 24: 677-736]; [Musumeci, G. and Minichiello, L. (2011); BDNF-TrkB signalling in fear learning: from genetics to neural networks, *Rev. Neurosci.*, 22(3):303-15]; [Xiao, J. et al. (2009); The role of neurotrophins in the regulation of myelin development, Neurosignals, 17: 265-276] and [Von Bohlen and Halbach, O. (2011); Immunohistological markers for proliferative events, gliogenesis, and neurogenesis within the adult hippocampus, Cell Tissue Res., 345(1):1-19].

The CNS develops starting early after conception, throughout gestation and continues to mature until early adulthood. In particular, structural maturation is mostly pre-natal while functional network maturation is mostly post-natal. In human fetuses, the cerebral cortex develops quite late and over a protracted period of time.

In utero, there is a peak of neuronal/brain maturation and growth from week 30 of gestation in humans.

The development of GABAergic functions, including the capacity to filter information, in particular sensory information such as visual signals, is a crucial step in the development of the cognitive functions in mammals, in particular in infants and young children. Although such development and improvement of GABAergic functions is of particular importance during the first months/years of life (where the neuronal plasticity is the highest), it can also affect older subjects, teenagers and adults, or elderly or diseased subjects.

Premature babies by definition enter the world with a still primitive brain, indeed they exhibit very basic electrical activity in the primary sensory regions of the cerebral cortex—those areas that perceive touch, vision, and hearing, as well as in primary motor regions of the cerebral cortex. For these babies the post-natal gradual maturation of the brain is essential to compensate for their lower brain maturation status at birth, this compensatory maturation is particularly important for the more complex part of the brain that mediates much of their emotional, social and cognitive maturation in the first few years of life [Lubsen, J. et al. (2011); Microstructural and functional connectivity in the developing preterm brain, Seminars in Perinatology, 35, 34-43].

Preterm babies are born at a time that is crucial for structural and functional brain development and maturation and, so, they miss out on in utero brain development. They are at risk for medical conditions after birth, including hemorrhagic and hypoxic-ischemic brain injuries, as well as for development problems later in life, including cognitive deficits. This risk seems to be higher the younger the babies are delivered and the lower their birth weight is. Cognitive deficits in terms of lower IQ, lower attention and working memory abilities, and problems in executive functions may persist into school-age and adolescence [Talge, N. et al. (2010). Late-Preterm Birth and its Association with Cognitive and Socioemotional Outcomes at 6 Years of Age. Pediatrics, 126, 1124-1131; van Baar, A., et al. (2009). Functioning at school age of moderately preterm children born at 32 to 36 weeks' gestational age. Pediatrics, 124, 251-257; Farooqi, A et al. (2011). Impact at age 11 years of major neonatal morbidities in children born extremely preterm. Pediatrics, 127, e1247-1257; Nosarti, C. et al. (2010). Neurodevelopmental outcomes of preterm birth. Cambridge: Cambridge University Press].

More generally CNS immaturity or delayed maturation of the CNS, can be observed in infants such as:

Preterm infants, low birth weight (<2500 g), very low and extremely low birth weight infants (<1500 g), extremely low birth weight (<1000 g) and in small for gestational age infants [Allen, M. C. (2008); Neurodevelopmental outcomes of preterm infants, *Curr. Opin Neurol.*, 21(2): 123-8].

Premature or term-born infants having experienced an intrauterine growth retardation (IUGR) that occurred following any adverse events during the gestation (smoking of the mother, medication of the mother, low placenta quality, abnormal placenta positioning, malnutrition of the mother and the foetus, excessive stress/anxiety of the mother, etc); [Gregory, A. et al. (2008); Intrauterine Growth Restriction Affects the Preterm Infant's Hippocampus, *Pediatric Research,* 63(4): 438-443].

Any neonate and young infant showing nervous system growth retardation following, for example, hypoxemia-ischemia at birth, postnatal complications, postnatal steroid treatments or any other adverse event (see for example Barrett, R. D. et al. (2007); Destruction and reconstruction: hypoxia and the developing brain, *Birth Defects Res. C. Embryo Today,* 81: 163-76).

Cognitive dysfunctions are reported in these infants, along with dysfunction in their growth and development, indicating that an optimal "catch-up" of the neurodevelopmental process is not achieved. Immaturity or delayed maturation of the cerebral cortex can lead to delayed and/or impaired learning ability, information integration, processing of sensory input, loss of, or poor development of higher reasoning, executive functions, concentration, attention, motor skills and language. This may lead to behavioral problems abnormally low intelligence, and thus, abnormally low mental performance.

It has been generally observed that breastfeeding preterm infants can result in improved neurodevelopment compared to formula feeding. (See for example: Rozé et al. The apparent breastfeeding paradox in very preterm infants: relationship between breast feeding, early weight gain and neurodevelopment based on results from two cohorts, EPIPAGE and LIFT. *BMJ Open* 2012; 2:e000834).

In healthy population, it has been observed that breastfeeding infants can result in improved cognitive function and educational attainment in adulthood compared to formula feeding. (see for example: Victoria et al. Association between breastfeeding and intelligence, educational attainment, and income at 30 years of age: a prospective birth cohort study from Brazil. Lancet 2015)

According to the inventors, this tends to indicate that some nutrients present in the human breast milk may be missing from conventional/generic synthetic formula or delivered in a sub-optimal amount. There is a need to identify the key differences between conventional formula and human breast milk and adapt the synthetic formula accordingly.

Behavioral and neurodevelopmental disorders associated with delayed maturation of the cerebral cortex, in particular pathological GABAergic functions, include attention deficit/hyperactivity disorders, autism spectrum disorders, as well as schizophrenia.

Cognitive function may be measured in humans with clinical tests that depend on age; many such tests known to pediatricians and child development experts. For babies and infants, development screening and neurodevelopment tests exist such as for example, BSID—Bayley Scales of Infant Development, Brazelton Neonatal Behavioral Assessment Scale, NEPSY—A Developmental NEuroPSYchological Assessment and Griffiths Mental Development Scales. For pre-school and/or school children tests for cognitive abilities include PPVT (Peabody Picture Vocabulary Test), TONI-2 (Test of Nonverbal Intelligence-2), WPPSI (Wechsler Preschool and Primary Scales of Intelligence), and CPM (Raven's Coloured Progressive Matrices).

It is known that nutrition plays an important role in neuronal maturation in the brain (reviewed in Huppi, P. S. (2008); Nutrition for the Brain, *Pediatric Research,* 63(3): 229-231 and Cusik and Georgieff (2016); The Role of Nutrition in Brain Development: The Golden Opportunity of the "First 1000 Days", *Journal of Pediatrics,* 175:16-21).

The consequences of malnutrition can be irreversible and may include poor cognitive development, poor memory, educability, and thus future economic productivity. (see for example Horton, R; (2008) The Lancet, Vol. 371, Issue 9608, page 179; Laus, M. F. et al. (2011); Early postnatal protein-calorie malnutrition and cognition: a review of human and animal studies, *Int. J. Environ. Res. Public Health.,* 8(2): 590-612).

While is it known that breast milk of mothers provides the best nutritional support to the developing brain, when breastfeeding is not possible, there is a need to provide synthetic nutritional compositions (such as infant formula or follow on formula) that induce an improvement or promote the development of optimal cognitive functions.

Thus, oral interventions are an appropriate way to positively impact on the development of the nervous system, so as to ensure optimal development of cognitive function, memory and mental performance in the preterm or term born neonates, infants, toddlers, children or young adults or young animals.

However little is known and has so far been proven, on the capacity of nutritional diets or nutritional compositions to influence the development or the promotion of GABAergic functions, and especially in infants and young children.

Thus, there is a need to promote and support the healthy establishment of cognitive function in general and to improve, enhance, promote or modulate a GABAergic function in the CNS, in particular filtering of information or the capacity to focus or concentrate on a mental or physical activity.

There is a need to avoid, prevent or compensate attention deficit/hyperactivity disorders, autism spectrum disorders, as well as schizophrenia, especially in subjects in needs thereof, and especially by promoting or modulating the GABAergic functions in the CNS.

There is a need to promote the development or improve such functions in young subjects, particularly infants and young children such as a human infant or young children, preterm or not, between birth and 7 years.

There is a need to provide such nutritional intervention and/or prophylactic nutritional intervention in a form that is well accepted by the subject population, in particular those of in these populations that are the most fragile or the most in need. There is a further need to not induce disadvantages, side-effects or negatives in such population.

There is a need to provide such solutions to the subject populations in the most simple and most cost-effective way, preferably not through the use of actual ingredients considered as drugs or medicaments, and preferably as part of the diet.

The present invention applies to all mammals, including animals and humans and in particular in infants, young children or young pets for which the brain plasticity is highest. The preferred target group is human (preterm or term) infants or young children/pets between birth and 7 years.

SUMMARY OF THE INVENTION

The present inventors have found surprisingly that the administration of a specific oligosaccharide or a mixture of specific oligosaccharides comprising HMO, alone or in combination with OF and/or BMOS is particularly effective in improving, enhancing, promoting or modulating a GABAergic function in the CNS, or filtering of information or the capacity to focus or concentrate on a mental or physical activity. The administration of said oligosaccharides can be done as part of a nutritional intervention or as a therapeutical intervention in subjects in need thereof.

DETAILED DESCRIPTION OF EXEMPLARY EMBODIMENTS

Definitions

As used herein, the following terms have the following meanings.

The term "infant" means a child under the age of 12 months.

The term "young child" means a child aged between one and seven years.

The articles "a" and "an", as used herein, preceding an element or component are intended to be nonrestrictive regarding the number of instances (i.e. occurrences) of the element or component. Therefore, "a" or "an" includes one or at least one, and the singular word form of the element or component also includes the plural unless the number is obviously meant to be singular.

The term "human milk oligosaccharide" is abbreviated HMO and collectively refers to those oligosaccharides that are present in human milk, and falls into the conventional definition adopted by any person in the art. HMOs comprise but are not limited to, fucosylated oligosaccharides (such as 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof), N-5 acetylated oligosaccharides (such as lacto-N-tetraose (LNT), N-neotetraose (LNnT) and any combination thereof), and sialylated oligosaccharides.

The term "bovine milk oligosaccharide" (abbreviated BMO) refers to those oligosaccharides that are present in bovine milk, and falls into the conventional definition adopted by any person in the art. The BMOs mixture used in the context of the present invention can, for example, be derived from bovine milk whey. Briefly, an ultrafiltration permeate of bovine whey including oligosaccharides such as 3'- and 6'-sialyllactose and GOS can be demineralised by a combination of electrodialysis and ion exchange, as described in the art. BMO can comprise, but are not limited to fucosylated oligosaccharides (such as 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof), N-5 acetylated oligosaccharides (such as lacto-N-tetraose (LNT), N-neotetraose (LNnT) and any combination thereof), and sialylated oligosaccharides.

The term "oligofructose" (abbreviated OF) as used herein refers to a fructose oligomer (i.e. a fructose oligosaccharide) having a degree of polymerization of from 2 to 10, for example a degree of polymerization of from 2 to 8. OF can also be referred as fructose oligosaccharide or Fructo-Oligo-Saccharides (abbreviated FOS) or short-chain Fructo-Oligo-Saccharides (abbreviated scFOS). In the present disclosure, the terms OF, FOS, scFOS have the same meaning and can be used interchangeably.

Inulin, comprising polymers of long chains are specifically excluded from the present definition of OF. OF is distinguishable from Inulin by its degree of polymerization (Inulin having much longer chains).

FOS/scFOS/OF is typically commercially available, for example under the commercial name ORAFTI Oligofructose by Beneo GmbH (Mannheim, Germany) (for example ingredient Orafti® P95).

The term "sialylated oligosaccharide" means an oligosaccharide having one or more sialic acid residues.

The term "fucosylated oligosaccharide" means an oligosaccharide having one or more fucose residues.

The term "sn-2 palmitate" as used herein refers to palmitic acid in the sn-2 position of the triglyceride to which it is bonded.

Gamma-aminobutyric acid or "GABA" is commonly known as an inhibitory neurotransmitter in the CNS and for its function to inhibit neuronal activity involved, for example, in synchronizing network of neurons in the hippocampus. The term "GABAergic" means "pertaining to or affecting the neurotransmitter GABA". For instance, a synapse is GABAergic if it uses GABA as its neurotransmitter. In another example, a GABAergic neuron can produce GABA. In another example, a substance is GABAergic if it is capable of eliciting effects via interactions with the GABA system, such as by stimulating or blocking neurotransmission. In another example, a GABAergic or GABAergic agent is any chemical that is capable of modifying the effects of GABA in the body or brain. Classes of GABAergic drugs include, but are not limited to, GABA receptor agonists, GABA receptor antagonists, and GABA reuptake inhibitors. A specific, exemplary GABA receptor is GABA type B receptor (GABBR).

The term "GABAergic function in the central nervous system (CNS)", as used herein, pertains to any GABAergic function exerted by or on any cell, part of a cell, cellular receptor, system or circuit of cells comprised in the CNS, including but not limited to neurons and neuroglia such as astrocytes, oligodendrocytes, microglia and ependymal cells, for example involving GABAergic neurotransmission, GABA transport or GABA uptake. GABAergic neurotransmission is fundamental for filtering incoming information in the CNS, thereby limiting, reducing or removing unwanted or unnecessary information. Therefore, a particular GABAergic function in the CNS comprises functions in filtering of information or the capacity to focus or concentrate on a mental or physical activity. Multiple examples of GABAergic modulation of information filtering have been demonstrated in the art. For instance, hippocampal GABA content correlated with the capacity to inhibit retrieval of unwanted memory triggered by reminders in humans (Schmitz et al. Nat Commun. 2017, 8(1):1311). In the optic tectum of zebrafish, GABAergic interneurons are necessary for spatial filtering allowing the fishes to target adequately small prey (Del Bene et al. Science 2010, 330(6004):669-673). Further, alteration of striatal GABA levels via astrocyte uptake has been shown to modulate the information filtering properties of neurons (Goubard et al. J Physiol 2011, 589(9):2301-2319). Improving, enhancing, promoting or modulating of GABAergic functions in the CNS, can be assessed, e.g., by measuring expression levels of known genes involved in the GABAergic system, such as GABAergic receptors or transporters. For instance, hippocampal gene expression can be indicative of improved, enhanced, promoted or modulated GABAergic functions.

The term "nutritional composition" means a composition which nourishes a subject. This nutritional composition is usually to be taken orally or intravenously, and it usually includes a lipid or fat source and a protein source. Preferably the nutritional composition is a complete nutrition mix that fulfils all or most of the nutritional needs of a subject (for example an infant formula). Nutritional compositions comprise foodstuffs.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

Infant formula follow on formula and starter infant formula can either be in the form of a liquid, ready-to-consumer or concentrated, or in the form of a dry powder that may be reconstituted to form a formula upon addition of water. Such formulae are well-known in the art.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk is substituted by other food in the diet of an infant.

The term "synthetic mixture" means a mixture obtained by chemical and/or biological means, which can be chemically identical to the mixture naturally occurring in mammalian milks.

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen 8, Ouwehand A. Benno Y. et al. *"Probiotics: how should they be defined"* Trends Food Sci. Technol. 1999:10 107-10).

All percentages are by weight unless otherwise stated.

When the ingredients amounts are provided for as weight of ingredient/weight of powder nutritional composition is also intended that the invention comprises also the corresponding amount by litre taking in to account a dilution factor of the dry powder nutritional composition of 130 g/L (or a specified otherwise in the dilution instructions).

Human Milk Oligosaccharides:

HMOs are, collectively, the third largest solid constituents in human milk, after lactose and fat. HMO usually consists of lactose at the reducing end with a carbohydrate core that often contains a fucose or a sialic acid at the non-reducing end. There are more than one hundred milk oligosaccharides that have been isolated and characterized, however these represent only a very small portion of the total number remaining to be characterized.

Infant formulae can be developed using HMO ingredients, such as fucosylated oligosaccharides, in particular 2FL, lacto-N-tetraose, lacto-N-neotetraose, or sialylated oligosaccharides, for different purposes.

EP0975235B1 from Abbott Laboratories describes a synthetic nutritional composition comprising one or more HMOs, wherein the HMOs in the composition are chosen among a group of eight HMOs (3-fucosyllactose, lacto-N-fucopentaose III, lacto-N-fucopentaose II, difucosyllactose, 2'-fucosyllactose, lacto-N-fucopentaose I, lacto-N-neotetraose and lacto-N-fucopentaose V) wherein said composition is intended for cases of normal, healthy infants, children, adults or individuals having specialized needs such as those that accompany certain pathological conditions. EP0975235B1 states that, generally speaking, oligosaccharides protect infants from viral and bacterial infections of the respiratory, gastrointestinal and uro-genital tracts.

In one embodiment, the composition of the present invention contains a HMO selected from the group consisting of fucosylated oligosaccharides such as 2'-fucosyllactose (2FL), sialylated oligosaccharides and/or a N-acetyl-lactosamine such as lacto-N-neotetraose (LNnT) or lacto-N-tetraose (LNT) or a combination thereof. Compositions comprising 2FL are experimentally exemplified herein.

N-Acetyl-Lactosamine

In some embodiments the composition of the invention contains at least one N-acetyl-lactosamine. That is to say that the composition according to the invention contains N-acetyl-lactosamine and/or an oligosaccharide containing N-acetyl-lactosamine. Suitable oligosaccharides containing N-acetyl-lactosamine include lacto-N-tetraose (LNT) and lacto-N-neotetraose (LNnT).

Thus, in a preferred embodiment, the N-acetyl-lactosamine is preferably selected from the group comprising lacto-N-tetraose (LNT) and lacto-N-neotetraose (LNnT).

LNT and LNnT may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably the composition according to the invention contains from 0.1 to 3 g N-acetyl-lactosamine per 100 g of composition on a dry weight basis. Preferably it contains 0.1 to 3 g of LNnT per 100 g of composition on a dry weight basis.

In one embodiment the nutritional composition according the invention comprises a N-acetyl-lactosamine, preferably selected from the group comprising lacto-N-tetraose (LNT) and lacto-N-neotetraose (LNnT).

Sialylated Oligosaccharides

The composition according to the invention, in some embodiments, can comprise one or more sialylated oligosaccharides.

Sialylated oligosaccharides include all sialylated HMO, including 3'-sialyllactose and 6'-sialyllactose. Preferably, both 3'-sialyllactose and 6'-sialyllactose are present in said composition. In this embodiment, the ratio between 3'-sialyllactose and 6'-sialyllactose lies preferably in the range between 100:1 and 1:100, more preferably 10:1 and 1:10, even more preferably 5:1 and 1:2.

The 3'- and 6'-forms of sialyllactose may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

Preferably the composition according to the invention contains from 0.05 to 10 g, more preferably 0.1 to 5 g, even more preferably 0.1 to 2 g of sialylated oligosaccharide(s) per 100 g of composition on a dry weight basis.

In one embodiment the nutritional composition according the invention comprises sialylated oligosaccharide, preferably selected from the group comprising 3'-sialyllactose and 6'-sialyllactose. More preferably said composition comprises both 3'-sialyllactose and 6'-sialyllactose, the ratio between 3'-sialyllactose and 6'-sialyllactose lying preferably in the range between 100:1 and 1:100, more preferably 10:1 and 1:10, even more preferably 5:1 and 1:2.

Fucosylated Oligosaccharide

The composition according to the invention may comprise one or more fucosylated oligosaccharides. Preferably the fucosylated oligosaccharides consist or comprises 2'-fucosyllactose (2-FL).

The fucosylated oligosaccharide may be selected from the group comprising 2'-fucosyllactose, 3-fucosyllactose, difucosyllactose (DiFL), lacto-N-fucopentaoses (that is to say lacto-N-fucopentaose I, lacto-N-fucopentaose II, lacto-N-fucopentaose III and lacto-N-fucopentaose V), lacto-N-difucohexaose I, fucosyllacto-N-hexaose, Difucosyllacto-N-hexaose I and Difucosyllacto-N-neohexaose II. A particularly preferred fucosylated oligosaccharide is 2'-fucosyllactose (2-FL) or DiFL.

The fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa Hakko Kogyo of Japan.

Preferably, the composition according to the invention contains from 0.1 to 3 g of fucosylated oligosaccharide(s) per 100 g of composition on a dry weight basis, most preferably being 2FL.

In one embodiment the nutritional composition according the invention comprises a fucosylated oligosaccharide, preferably selected from the group comprising 2'-fucosyllactose, 3-fucosyllactose, difucosyllactose, lacto-N-fucopentaoses (that is to say lacto-N-fucopentaose I, lacto-N-fucopentaose II, lacto-N-fucopentaose III and lacto-N-fucopentaose V), lacto-N-difucohexaose I, fucosyllacto-N-hexaose, Difucosyllacto-N-hexaose I and Difucosyllacto-N-neohexaose II, and preferably the fucosylated oligosaccharide is 2'-fucosyllactose (2-FL).

Further Prebiotics

Additional to the essential oligosaccharides of the present patent claims, the composition of the invention can further comprise at least one or one further prebiotic, usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria.

The composition according to the invention can comprise, in some embodiments, Oligofructose (OF). An example of such OF is the commercial ingredient ORAFTI® by Beneo GmbH (Mannheim, Germany).

In some embodiments the prebiotics of the composition of the invention, comprise other fructooligosaccharides (FOS) or/and galactooligosaccharides (GOS). A combination of prebiotics may be used such as 90% GOS with 10% short chain fructo-oligosaccharides such as in the product by BENEO-Orafti sold under the trademark "Orafti® oligofructose" (previously Raftilose®) or 10% inulin such as in the product sold by BENEO-Orafti under the trademark "Orafti® inulin" (previously Raftiline®). Another combination of prebiotics is 70% short chain fructo-oligosaccharides and 30% inulin, which is a product sold by BENEO-Orafti® under the trademark "Prebio 1".

In one embodiment the nutritional composition according the invention comprises a prebiotic selected from the list bovine milk oligosaccharides, inulin, xylooligosaccharides, polydextrose or any combination thereof.

In one embodiment, the nutritional composition according the invention comprises a bovine milk oligosaccharide (BMO). The BMO can comprise oligosaccharides being an N-acetylated oligosaccharide, a galacto-oligosaccharide, a sialylated oligosaccharide, a fucosylated oligosaccharide or a combination thereof.

Probiotics

The composition of the invention can further comprise at least one probiotic. Non limiting examples of probiotics include: *Bifidobacterium*, *Lactobacillus*, *Lactococcus*, *Enterococcus*, *Streptococcus*, *Kluyveromyces*, *Saccharoymces*, *Candida*, in particular selected from the group consisting of *Bifidobacterium longum*, *Bifidobacterium lactis*, *Bifidobacterium animalis*, *Bifidobacterium breve*, *Bifi-* dobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii or mixtures thereof, preferably selected from the group consisting of Bifidobacterium longum NCC3001 (ATCC BAA-999), Bifidobacterium longum NCC2705 CNCM I-2618), Bifidobacterium longum NCC490 (CNCM I-2170), Bifidobacterium lactis NCC2818 (CNCM I-3446), Bifidobacterium breve strain A, Lactobacillus paracasei NCC2461 (CNCM I-2116), Lactobacillus johnsonii NCC533 (CNCM I-1225), Lactobacillus rhamnosus GG (ATCC53103), Lactobacillus rhamnosus NCC4007 (CGMCC 1.3724), Enterococcus faecium SF 68 (NCC2768; NCIMB10415), and combinations thereof.

In one embodiment, said probiotic is a probiotic bacterial strain, preferably Bifidobacteria and/or Lactobacilli. Suitable probiotic bacterial strains include Lactobacillus rhamnosus ATCC 53103 available from Valio Oy of Finland under the trademark LGG, Lactobacillus rhamnosus CGMCC 1.3724, Lactobacillus paracasei CNCM I-2116, Lactobacillus johnsonii CNCM I-1225, Streptococcus salivarius DSM 13084 sold by BLIS Technologies Limited of New Zealand under the designation KI2, Bifidobacterium lactis CNCM 1-3446 sold inter alia by the Christian Hansen company of Denmark under the trademark Bb 12, Bifidobacterium longum ATCC BAA-999 sold by Morinaga Milk Industry Co. Ltd. of Japan under the trademark BB536, Bifidobacterium breve sold by Danisco under the trademark Bb-03, Bifidobacterium breve sold by Morinaga under the trade mark M-16V, Bifidobacterium infantis sold by Procter & Gamble Co. under the trademark Bifantis and Bifidobacterium breve sold by Institut Rosell (Lallemand) under the trademark R0070.

Preferably, the composition according to the invention contains from 10e3 to 10e12 cfu of probiotic bacterial strain, more preferably between 10e7 and 10e12 cfu, per g of composition on a dry weight basis.

In one embodiment the nutritional composition of the comprises a probiotic bacterial strain selected from the list consisting of Lactobacillus acidophilus, Lactobacillus salivarius, Lactobacillus rhamnosus, Lactobacillus paracasei, Lactobacillus casei, Lactobacillus johnsonii, Lactobacillus plantarum, Lactobacillus fermentum, Lactobacillus lactis, Lactobacillus delbrueckii, Lactobacillus helveticus, Lactobacillus bulgari, Lactococcus lactis, Lactococcus diacetylactis, Lactococcus cremoris, Streptococcus salivarius, Streptococcus thermophilus, Bifidobacterium lactis, Bifidobacterium animalis, Bifidobacterium longum, Bifidobacterium breve, Bifidobacterium infantis, or Bifidobacterium adolescentis or any mixture thereof.

Target Population

In one embodiment, the present invention targets/is for mammalian subjects. Preferably the mammals are human, or pets such as a dog or cat.

In a more preferred embodiment, the present invention is for young mammals, such as a young human, e.g., infants (for example 0 to 6 months or 0 to 12 months) or young children (for example 1 to 3 years or 1 to 7 years), or young dogs (for example puppies) or young cats. In an even more preferred embodiment, the mammal is an infant or a young child. Without to be bound by the theory the young mammals have a high brain plasticity and brain (or brain connectivity) development and benefit most of the present invention. It is also contemplated that the present invention may target particular windows of nutritional intervention (for example such as children 6 months to 3 years, 3 months to 18 months), subpopulations having particular need (fragile young mammals; senile or semi-senile mammals) or in a recovery phase. In one embodiment, the present invention is especially targeted to subjects in needs of avoidance, prevention or compensation of attention deficit/hyperactivity disorders, autism spectrum disorders, as well as schizophrenia (for example mammals born preterm or with suboptimal growth or development). In one embodiment the present invention is especially targeted at subjects suffering from a health status or a disease related to GABAergic functions, in particular psychiatric or neurologic disorders related to GABAergic functions such as filtering of information or the capacity to focus or concentrate on a mental or physical activity. Such disease can comprise psychiatric or neurological disorders such as attention deficit/hyperactivity disorders, autism spectrum disorders, as well as schizophrenia.

According to a preferred embodiment, the composition according to the invention is for use in healthy infants and/or healthy young children. In one embodiment the invention is of particular relevance in fragile infants, preterm infants, and/or infant born with a subnormal birth weight and/or infants subject of intrauterine growth retardation. The preferred period of use is during the period(s) of most rapid development of the memory and/or development of the brain connectivity.

The composition of the invention is targeted to infants and/or young children, of age 7 years or less, preferably of age 3 years or less, most preferably age 1 year of less. In one embodiment the composition is intended for infants of 6 months or less. In embodiments of the invention the composition is used during the first 6 months of life, first 1 year of life, first 3 years of life, first 7 years of life, and/or during a period of recovery after sickness or of low development.

Nutritional Composition

The nutritional composition according to the invention is preferably a synthetic nutritional composition. The composition of the invention can for example be a starter infant formula, an infant formula, a baby food, an infant cereal composition, a follow-on formula or a growing-up milk, and said composition is preferably a starter infant formula. The composition according to the invention can also be for use before and/or during a weaning period. In one embodiment the nutritional composition may be a complete nutritional composition or a supplement for aging, elderly or fragile persons.

The composition according to the invention can be completed composition provide 100% or a majority of the nutritional needs of the target populations (for example in term of caloric needs; or in terms of vitamin or minerals needs, in in term of protein, lipids or carbohydrate needs). Alternatively the composition of the invention can be a supplement to be consumed in addition to a regular diet). In that case however the dosage and overall consumption of the composition is adapted to provide the claimed benefit on the filtering of information (for example proportionally to the caloric load and to the subject caloric needs).

The use of a composition of the invention can encompass cases where the composition is a supplement, preferably provided in the form of unit doses. In one embodiment the composition is a supplement to human breast feeding.

The composition can be in the form of a powder composition for example intended to be diluted with water or mixed with milk (for example human breast milk), or ingested as a powder. In one embodiment the composition of the invention is in liquid form; either ready-to-drink or to be diluted in water or mixed with milk (for example human breast milk).

The composition according to the invention can also contain a protein source, preferably in an amount below 2.5 g/100 kcal or below 2.0 g per 100 kcal, even more preferably in an amount below 1.8 g per 100 kcal. In one embodiment the protein content is below 1.6 g/100 kcal. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

The composition according to the present invention generally contains a carbohydrate source. This is particularly preferable in the case where the nutritional composition of the invention is an infant formula. In this case, any carbohydrate source conventionally found in infant formulae such as lactose, saccharose, maltodextrin, starch and mixtures thereof may be used although the preferred source of carbohydrates is lactose.

The composition according to the present invention generally contains a source of lipids. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. The fat source preferably has a ratio of n-6 to n-3 fatty acids of about 5:1 to about 15:1; for example about 8:1 to about 10:1.

The composition of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, and the like.

In one embodiment, the composition of the invention, especially in the form of an infant formula, comprises from about 1.8 to about 2.2 g of total protein per 100 kcal, for example, about from 1.8 to about 2.1 g or from about 1.9 to about 2.1 g protein per 100 kcal, optionally wherein from about 0.3 to about 0.4 g/100 kcal of protein is alpha-lactalbumin. The infant formula and follow-on formula of this invention may be in the form of a ready-to-feed liquid, or may be a liquid concentrate or powdered formula that can be reconstituted into a ready-to-feed liquid by adding an amount of water that results and follow-on formula of this invention includes all the ingredients that are required by law in the US or EU, including but not limited to certain vitamins, minerals, and essential amino acids. It may also include nucleotides, such as CMP, UMP, AMP, GMP and IMP, lutein, zeaxanthin, and other ingredients known in the art.

In one embodiment of the invention the nutritional composition is a pet food (for example for dogs or cats or young dogs or young cats).

Effect(s) and Use of the Composition of the Invention

The present invention relates to improving, enhancing, promoting or modulating a GABAergic function in the CNS of a subject. This can include improving, enhancing, promoting, or modulating filtering of information or the capacity to focus or concentrate on a mental or physical activity.

Without to be bound by the theory, in one aspect of the invention such improvement, enhancement and/or promotion is believed to be linked to the effect of the oligosaccharide of the invention on the gut microbiota. Oligosaccharides such as HMO (e.g., 2FL or LNnT), BMO or OF are only slightly digested in the small intestine, thus the majority becomes available for fermentation by microbiota in the colon. Indeed, HMO (e.g., 2FL or LNnT), BMO or OF have been shown to promote the growth of intestinal bifidobacteria as reflected by an increase in this family of bacteria in the stools in infants fed Oligosaccharides-supplemented formulas, comprising HMO (e.g., 2FL or LNnT), BMO or OF. It appears that both oligosaccharides and probiotics are linked to beneficial alteration of GABA receptor expression in the brain. Without wishing to be bound by any theory, due to the high presence of GABA in some bacterial species (e.g., *Lactobacillus* and *Bifidobacterium*), such probiotic species may act as delivery vehicles for GABA, and their intake may exert local effects on the gastrointestinal system that ultimately modulate host neurophysiology (Lyte, BioEssays 2011, 33, 574-581). This connection appears even stronger given prokaryotes and eukaryotes both synthesize GABA via decarboxylation of glutamate via glutamate decarboxylase (GAD), and analyses from the Human Microbiome Project suggests genes encoding GAD are present in the human microbiome (Mazzoli, R., and Pessione, E. (2016). Front. Microbiol. 7, 1934; Pokusaeva et al., Neurogastroenterol. Motil. 2017, 29(1) doi:10.1111/nmo.12904).

In short, the present nutritional composition may be used in improving, enhancing, promoting or modulating a GABAergic function via its effect on gut microbiota and gut-brain axis which has been shown in influencing many aspects of brain functioning. One could also contemplate that the improving, enhancing, promoting or modulating a GABAergic function may be related to an increase the sialic acid (Neu5Ac) concentration in the brain of said individual, mediated by differential metabolic pathways influenced by the gut microbiota. Without being bound by theory, in one embodiment of the invention, the HMO synergistically act with a probiotic and the endogenous microbiota to best influence such metabolic pathways.

In another aspect, an effect underlying the invention can be linked to altered gene expression of GABAergic genes in the CNS of a subject, in particular GABA receptors or GABA transporters. In one embodiment, altering refers to measured increased or decreased gene expression levels at the mRNA or protein level in comparison to a control. In one embodiment, gene expression refers to hippocampal gene expression of a subject.

In another aspect, an effect underlying the invention can be linked to the enhancement of the neuroplasticity in the brain of the subject, and/or by enhancing neurodevelopment, neurogenesis, axonal sprouting, myelination and/or maturation in the brain of said subject (without to be bound by the theory).

GABAergic functions, and particular the capacity of information filtering or focusing on a mental or physical activity represents essential aspects of the brain function and development and are crucial for the overall cognitive development of the subject. It influences in particular the processing, classification and management of external signals, the learning ability as well as spatial orientation.

In one embodiment of the present invention, the GABAergic function is the capacity of filtering information, for instance incoming sensory information. Filtering of information is of capital importance in the social and cognitive development, especially of young subjects. In one embodiment of the present invention, the GABAergic function is the capacity to focus or concentrate on a mental or physical activity Thus, in one aspect, the present invention relates to (or is defined by) the use of a nutritional composition comprising a HMO for improving, enhancing, promoting or modulating a GABAergic function in the CNS, in particular the capacity of filtering of information or the capacity to focus or concentrate on a mental or physical activity in a mammal.

In one aspect, the present invention relates to (or is defined by) the use of the herein described nutritional composition comprising a HMO for avoiding, preventing or compensating attention deficit/hyperactivity disorders, autism spectrum disorders, as well as schizophrenia, especially in subjects in needs thereof, and especially by promoting or modulating the GABAergic functions in the CNS.

In one aspect, the present invention relates to (or is defined by) the use of the herein described nutritional composition comprising a HMO for improving, enhancing or modulating attention deficit/hyperactivity disorders, autism spectrum disorders, as well as schizophrenia, and especially by promoting or modulating the GABAergic functions in the CNS.

In one aspect, the present invention relates to (or is defined by) the use of the herein described nutritional composition comprising a HMO for improving, enhancing or modulating a GABAergic function in the CNS, in particular, filtering of information or the capacity to focus or concentrate on a mental or physical activity.

In one embodiment the invention present relates to (or is defined by) the use of the herein described nutritional composition wherein said composition is an infant formula, follow on formula, human milk fortifier, growing up milk, or pet food.

In another aspect, the invention relates to (or is defined by) a HMO for use in improving, enhancing, promoting or modulating a GABAergic function in the CNS, in particular the capacity of filtering of information or the capacity to focus or concentrate on a mental or physical activity, in a subject in need thereof. In a specific embodiment, the subject is a mammal wherein said mammal is preferably a human, cat or dog and wherein said human is preferably an infant or a young child.

In another aspect, the invention relates to (or is defined by) a nutritional composition comprising a HMO for use in improving, enhancing, promoting or modulating a GABAergic function in the CNS, in particular the capacity of filtering of information or the capacity to focus or concentrate on a mental or physical activity, in a subject in need thereof. In a specific embodiment, the subject is a mammal, preferably said mammal being a young mammals, a human, a dog or a cat, more preferably a young human, dog or cat, most preferably an infant or young children. The nutritional composition can also comprise one or more of the optional ingredients described herein.

In another aspect, the invention present relates to (or is defined by) the use of HMO in the manufacture of a nutritional composition for improving, enhancing, promoting or modulating a GABAergic function in the CNS, in particular the capacity of filtering of information or the capacity to focus or concentrate on a mental or physical activity, in a subject in need thereof. In a specific embodiment, the subject is a mammal, preferably said mammal being a young mammals, a human, a dog or a cat, more preferably a young human, dog or cat, most preferably an infant or young children.

Dosage

HMO: In one embodiment, HMO is present in a total amount of from 0.01 to 50 g/L, 0.1 to 10 g/L, 0.3 to 5 g/L or 0.5 to 1 g/L, or 0.25 or 0.5 or 1 or 1.5 or 2 g/L.

BMO: In one embodiment, BMO is present in a total amount of from 0.01 to 50 g/L, 0.1 to 10 g/L, 0.3 to 5 g/L or 0.5 to 1 g/L, or 0.25 or 0.5 or 1 or 1.5 or 2 g/L.

Fructo oligosaccharide/FOS/OF: When present, the nutritional composition of the present invention may contain from 0.1 to 20 g of oligofructose (OF) per 100 g of composition on a dry weight basis, e.g. from 1 to 6 g or from 3 to 5 g of oligofructose (OF) per 100 g of composition on a dry weight basis.

The one embodiment of the invention the nutritional composition comprises an amount of fructose oligosaccharide in the following ranges or amount:

- 0.1 to 20 g/L or 0.5 to 10 g/L or 1 to 8 g/L or 2 to 6 g/L or 1.5 g/L or 3 g/L or 5 g/L of nutritional composition, when the composition is in a ready-to-feed liquid form, or
- 0.1 to 20 g/L or 0.5 to 10 g/L or 1 to 8 g/L or 2 to 6 g/L or 1.5 G/L or 3 g/L or 5 g/L (of the liquid diluted form) when the composition is in powder form and intended to be recomposed into a diluted liquid form, or
- the same as above multiplied by 2, 5, 10, 20, 50 or 100 when the nutritional composition is in the form of a concentrated composition intended to be diluted (respectively 2, 5, 10, 20, 50, or 100 times) into water or human breast milk or intended to be used directly as a concentrated form, or
- 0.4 g to 15 g/100 g of nutrition composition powder, or 0.8 to 10 g/100 g, or 1 to 6 g/100 g, or 2 to 5 g/100 g or 2.1 to 4 g/100 g or 1.2 g/100 g or 2.3 g/100 g or 3.8 g/100 g or 4 g/100 g or 6 g/100 g of nutrition composition powder, when the nutritional composition is in the form of a dry powder.

In one embodiment the OF content may be 0.07 g to 3 g/100 kcal of nutrition composition powder, or 0.1 to 2 g/100 kcal, or 0.4 to 1.5 g/100 kcal, or 0.45 to 1 g/100 kcal or 0.45 to 0.75 g/100 kcal or 0.3 g/100 kcal or 0.4 g/100 kcal or 0.5 g/100 kcal or 0.75 g/100 kcal or 1 g/100 kcal of nutrition composition powder, when the nutritional composition is in the form of a dry powder.

2FL: The nutritional composition of the present invention may contain from 0.02 to 10 g of 2FL per 100 g of composition on a dry weight basis, e.g. from 0.2 to 0.5 g or from 0.3 to 5 g of 2FL per 100 g of composition on a dry weight basis.

In one embodiment, the nutritional composition comprises an amount of 2FL in the following ranges or amount:

0.05 to 20 g/L or 0.1 to 5 g/L or 0.2 to 3 g/L or 0.1 to 2 g/L or 0.25 g/L to 1 g/L or 0.25 g/L or 1 g/L of nutritional composition, when the composition is in a ready-to-feed liquid form, or 0.05 to 20 g/L or 0.1 to 5 g/L or 0.2 to 3 g/L or 0.1 to 2 g/L or 0.25 g/L to 1 g/L or 0.25 g/L or 1 g/L (of the liquid diluted form) when the composition is in powder form and intended to be recomposed into a diluted liquid form, or the same as above multiplied by 2, 5, 10, 20, 50 or 100 when the nutritional composition is in the form of a concentrated composition intended to be diluted (respectively 2, 5, 10, 20, 50, or 100 times) into water or human breast milk or intended to be used directly as a concentrated form, or 0.04 g to 1.5 g/100 g of nutrition composition powder, or 0.08 to 1.2 g/100 g, or 0.1 to 1 g/100 g, or 0.2 to 0.8 g/100 g or 0.2 g/100 g or 0.4 g/100 g or 0.8 g/100 g or 1 g/100 g or 1 g/100 g of nutrition composition powder, when the nutritional composition is in the form of a dry powder.

In one embodiment the 2FL content may be 0.01 g to 0.3 g/100 kcal of nutrition composition powder, or 0.02 to 0.2 g/100 kcal, or 0.04 to 0.15 g/100 kcal, or 0.02 g/100 kcal or 0.04 g/100 kcal or 0.07 g/100 kcal or 0.15 g/100 kcal or 0.3 g/100 kcal of nutrition composition powder, when the nutritional composition is in the form of a dry powder.

LNnT: In one embodiment, the nutritional composition may contain from 0.01 to 1 g of LNnT per 100 g of composition on a dry weight basis, e.g. from 0.1 to 0.25 g or from 0.15 to 0.5 g of LNnT per 100 g of composition on a dry weight basis.

The one embodiment of the invention the nutritional composition comprises an amount of LNnT in the following ranges or amount:

0.02 to 10 g/L or 0.05 to 2.5 g/L or 0.1 to 1.5 g/L or 0.05 to 1 g/L or 0.12 g/L to 0.5 g/L or 0.12 g/L or 0.5 g/L or 1 g/L of nutritional composition, when the composition is in a ready-to-feed liquid form, or 0.02 to 10 g/L or 0.05 to 2.5 g/L or 0.1 to 1.5 g/L or 0.05 to 1 g/L or 0.12 g/L to 0.5 g/L or 0.12 g/L or 0.5 g/L or 1 g/L (of the liquid diluted form) when the composition is in powder form and intended to be recomposed into a diluted liquid form, or the same as above multiplied by 2, 5, 10, 20, 50 or 100 when the nutritional composition is in the form of a concentrated composition intended to be diluted (respectively 2, 5, 10, 20, 50, or 100 times) into water or human breast milk or intended to be used directly as a concentrated form, or 0.02 g to 0.75 g/100 g of nutrition composition powder, or 0.04 to 0.6 g/100 g, or 0.0.5 to 0.5 g/100 g, or 0.1 to 0.4 g/100 g or 0.1 g/100 g or 0.2 g/100 g or 0.25 g/100 g or 0.5 g/100 g or 1 g/100 g or 3 g/100 g of nutrition composition powder, when the nutritional composition is in the form of a dry powder.

In one embodiment the LNnT content may be 0.01 g to 0.3 g/100 kcal of nutrition composition powder, or 0.02 to 0.2 g/100 kcal, or 0.04 to 0.15 g/100 kcal, or 0.02 g/100 kcal or 0.04 g/100 kcal or 0.07 g/100 kcal or 0.15 g/100 kcal or 0.3 g/100 kcal of nutrition composition powder, when the nutritional composition is in the form of a dry powder.

The composition of the invention, in particular when in the form of an infant formula, can contain at least about 0.4 g of oligofructose of oligofructose per 100 kcal. In some embodiments, it contains from about 0.4 to about 0.9 g, from about 0.4 to about 0.7 g, from about 0.4 to about 0.5 g, from about 0.7 to about 0.8 g, or from about 0.7 to about 0.9 g, oligofructose per 100 kcal. The oligofructose has a degree of polymerization of from 2 to 10. In one embodiment, at least 90% of the oligofructose has a degree of polymerization of from 2 to 8.

In one embodiment the nutritional composition comprises 2FL and LNnT, preferably in an amount of 1 g/L 2FL and 0.5 g/L LNnT, or 0.5 g/L 2FL and 0.25 g/L LNnT, or from 0.25 g/L to 2 g/L 2FL and 0.1 to 1 g/L LNnT.

Method for Manufacturing the Nutritional Composition

The nutritional composition may be prepared in any suitable manner known in the art. For example commercial infant formula of follow-on formula can serve as a base composition to which is added the required amount of oligosaccharides (e.g. HMO such as 2FL, LNnT or else, OF, BMO), preferably in a dry form. Alternatively the oligosaccharide can be added as dry ingredient or liquid ingredient into a liquid premix that will serve as a base to manufacture the nutritional composition of the invention. The liquid mix can then be dried by any conventional means For example, it may be prepared by blending together a protein source, a carbohydrate source (different from the oligosaccharide combination of the present invention), and a fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The 3'-Siallylactose (3'-SL) and 6'-Siallylactose (6'-SL) will be added at this stage if the final product is to have a liquid form. If the final product is to be a powder, the 3'-Siallylactose (3'-SL) and 6'-Siallylactose (6'-SL) may likewise be added at this stage if desired. The liquid mixture is then homogenized, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger. Then, the liquid mixture may be cooled to between about 60° C. and about 85° C., for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point. The homogenized mixture is transferred to a suitable drying apparatus such as a spray dryer or freeze dryer and converted to powder. The powder should have a moisture content of less than about 5% by weight.

If a liquid composition is preferred, the homogenized mixture may be sterilized then aseptically filled into suitable containers or may be first filled into the containers and then retorted.

Particular Lipids

The composition of the invention can comprise selected lipids have particular effects.

Those lipids can in particular include DHA, ARA, linoleic acid or Sphingomyelin, preferably in an amount suitable to deliver actual brain health benefits and within the general regulatory requirements for the type of products (for example WHO recommendations for infant formula; CODEX or European directives on infant formula).

In some embodiments the composition of the invention comprises a relatively high level of sn2 palmitate or sphingomyelin. Those have been linked to optimum brain performance and development and can act synergistically with essential compounds of the composition of the invention.

Although feeding an infant a formula containing a high percentage of sn-2 palmitate (in absence of OF) helps to promote the growth of bifidobacteria in the colon, the combination of high sn-2 palmitate with oligofructose is thought to provide significantly superior growth of bifidobacteria in the colon of formula-fed infants. A significant reduction in the amount of potentially pathogenic bacteria can also be achieved. It has been discovered that feeding an infant a high sn-2 palmitate-containing infant formula containing from about 3 to about 5 g/L, or from about 0.4 to about 0.7 g/100 kcal, of oligofructose is more beneficial than feeding the infant the same formula without oligofructose. Without being bound by the theory such synergistic effect between OF and sn2 palmitate can also promote short term memory though in particular (but most probably not only) its effect on the microbiome of the subject and the population of bifidobacteria. "High Sn2 Palmitate" is to be understood as ingredients having a high % of the fatty acids (preferably more than 33% of the fatty acids) as palmitate in the sn2 position of the Triglycerides. Such ingredients are commercially available under the trade name BETAPOL® (Loders Croklaan, Wormerveer, Netherlands) or INFAT® (Advanced Lipids AB, Karlshamn, Sweden, joint venture of AAK B.V. (Zaandijk, Netherlands) and Enzymotec Inc, Morristown, USA).

Recent infant clinical studies have shown that nutritional formulas containing at least one omega 6 fatty acid and at least one omega 3 fatty acid in a ratio of from about 6 to about 1 increased DHA accretion in erythrocytes and plasma. A balanced ratio of about 6:1 of omega 6 fatty acid to omega 3 fatty acid may also provide long term health benefits including optimum brain and neurological development. Such balance will be achieved by formulating the present invention with vegetable oil fat sources that have omega 6 fatty acid content, such as, for example, soybean oil and sunflower oil, and omega 3 fatty acid content, for example, rapeseed, canola, flaxseed, chia, perlla or walnuts. A unique fat blend with 5 different oils will be used to achieve the modified fat blend.

The following examples are presented to illustrate certain embodiments and features of the present invention, but should not be construed as limiting the scope of this invention.

EXAMPLES

Example 1: Nutritional Composition Comprising HMO (2FL and/or LNnT)

A nutritional composition of the invention comprising HMO 2FL and/or LNnT and OF is given in Table 1 below. This composition is given by way of illustration only. The composition of Table 1 can be an infant formula. Alternatively is can be adapted to be a follow-on formula.

TABLE 1

| Nutrients | per 100 kcal | per liter |
|---|---|---|
| Energy (kcal) | 100 | 670 |
| Proteins (g) | 1.83 | 12.3 |
| Fats (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (ug RE) | 105 | 700 |
| Vitamin D (ug) | 1.5 | 10 |
| Vitamin E (mg TE) | 0.8 | 5.4 |
| Vitamin K1 (ug) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| 2FL (g) and/or | 0.04 or 0.15 | 0.25 or 1 |
| LNnT (g) | 0.01 or 0.07 | 0.1 or 0.5 |
| Oligofructose (OF) (g) (optional) | 0.45 or 0.75 | 3 or 5 |
| 3'-SL (g) (optional) | 0.22 | 1.46 |
| 6'-SL (g) (optional) | 0.05 | 0.33 |
| Ratio 3'-SL:6'-SL (optional) | 4.4:1 | 4.4:1 |
| BMOs (g) (optional) | 0.4 or 2 | 3 or 15 |

Example 2: Infant Formula Comprising HMO (2FL and/or LNnT), Optional BMOs and/or Oligofructose (OF)

A nutritional composition of the invention comprising HMO (2FL and/or LNnT), and optionally OF and/or BMO is given in Table 2 below. This composition is given by way of illustration only. The composition of Table 2 is an infant formula. Alternatively is can be adapted to be a follow-on formula.

Another example is based on commercial NAN and/or lactogen Infant formulae (from Nestlé, Switzerland) to which the specific oligosaccharides of the invention are added as in the amount stated below.

TABLE 2

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (70% OF, 30% insulin) (g) (For example Beneo- | 0.64 | 4.3 |

TABLE 2-continued

| Nutrient | per 100 kcal | per liter |
|---|---|---|
| Orafti ® P95 and Inulin Beneo-Orafti ®) (optional) | | |
| 2FL (g) and/or | 0.3 | 2 |
| LNnT (mg) | 30 | 200 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 3'sialyllactose (mg) (optional) | 30 | 200 |
| 6'sialyllactose (mg) (optional) | 6 | 40 |
| BMOs (g) (optional) | 0.9 | 6 |

Experimental Data

In a piglet study, we investigated the impact of various oligosaccharides comprising HMO (e.g. 2FL) with or without OF and/or BMOS on hippocampal gene expression. Thirty-six male piglet (12 per treatment group) were treated from 48 h post-farrowing until 33 days of life with either control (CON, Purina ProNurse Livestock Milk Replacer), HMO (CON+1.5 g/L HMO (composed of 1.0 g/L 2'FL+0.5 g/L LNnT), OF [CON+5 g/L OF], OF+HMO [CON+5 g/L OF+1.0 g/L HMO (2'FL), BMO (6.5 g/L of BMOs) or HMO+BMO (1.0 g/L 2'FL+0.5 g/L LNnT+6.5 g/L BMOs). All diets contained a formulation space of 8.0 g/L that was reserved for addition of dietary test articles. Piglets were fed at a rate of 285 mL and 325 mL of reconstituted diet per kg BW from PND 2-6 and PND 7-33, respectively. Piglets were euthanized on day 32 or 33 and hippocampal tissue was collected for analysis of mRNA expression.

The BMOs mixture used in the formulae was derived from bovine milk whey. Briefly, an ultrafiltration permeate of bovine whey including oligosaccharides such as 3'- and 6'-sialyllactose and GOS was demineralised by a combination of electrodialysis and ion exchange, as described in the art.

Hippocampal Gene Expression

Approximately 20 mg of hippocampal tissue were introduced in a Lysing Matrix D tube (MP Biomedicals, Santa Ana, California, USA), placed on ice, and 650 µL of lysis buffer (Agencourt RNAdvance Tissue Kit, Beckman Coulter, Indianapolis, Indiana, USA) was added. Tubes were agitated for 2×1 minute at speed 6 on FastPrep®-24 (MP Biomedicals, Santa Ana, California, USA), and 400 µL of lysate were then extracted using the Agencourt RNAdvance Tissue Kit (Beckman Coulter, Indianapolis, Indiana, USA) following the manufacturer's recommendations. RNA were quantified using the Quant-iT™ RiboGreen™ RNA Assay Kit (Invitrogen, Carlsbad, California, USA) on a Spectramax M2 (Molecular Devices, Sunnyvale, California, USA). RNA quality assessment was completed using a Fragment Analyzer 96 with Standard Sensitivity RNA Analysis Kit (15 nt) (Advanced Analytical Technologies, Inc., Ankeny, Iowa, USA). Relative mRNA copy number on 93 genes was quantified using the NanoString nCounter™ system (NanoString Technologies Inc., Seattle, Washington, USA) according to the manufacturer's instructions using 100 ng of RNA as the starting amount.

Results

Figure 1:
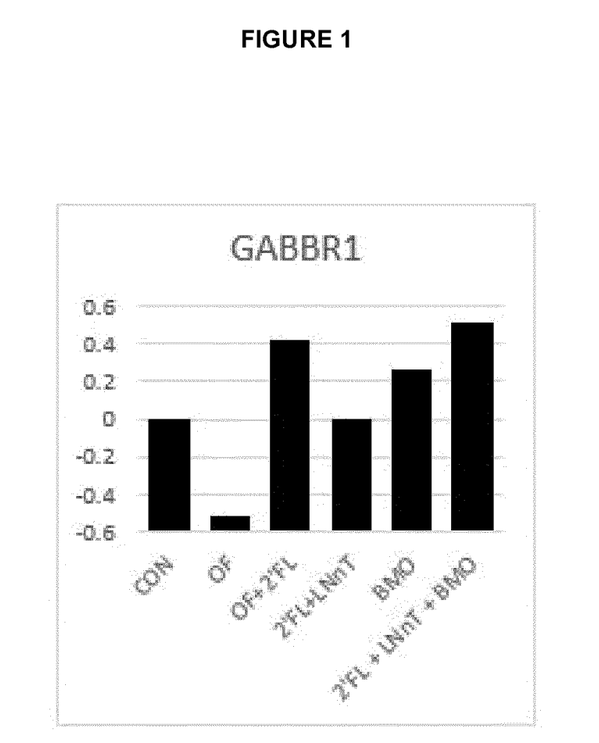
FIG. 1. Shown is the effect of various diets (HMO, BMO, HMO+BMO, OF, OF+HMO) in piglets on the hippocampal expression of the GABA receptor GABBR1. HMO, OF and BMO are as described in the examples.

The HMO, BMO, BMO+HMO and OF+HMO diets showed differential effects on gene expression compared to the CON group. Hippocampal mRNA expression of several key genes involved in the GABAergic system is shown in FIG. 1 for the GABA type B receptor subunit 1 (GABBR1) and in FIG. 2 for the GABA Type A Receptor Beta2 Subunit (GABRB2). Administering HMO, preferably in combination with a prebiotic such as OF and/or BMO has the surprising capability to modulate the GABAergic system at the expression level.

FIG. 1 shows that the mRNA expression of the GABBR1 receptor gene is either maintained or even significantly increased compared to the control diet (CON), when a HMO is also present in the test diet, either alone (2'FL+LNnt), or in combination with a OF or BMO.

Figure 2:
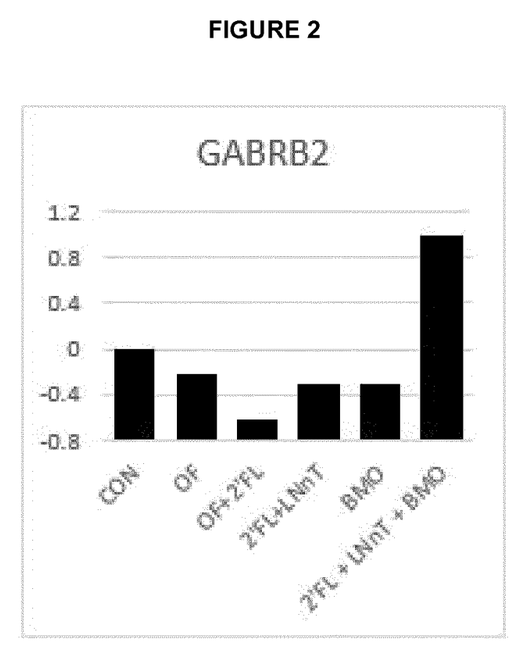
FIG. 2. Shown is the effect of various diets (HMO, BMO, HMO+BMO, OF, OF+HMO) in piglets on the hippocampal expression of the GABA receptor GABRB2. HMO, OF and BMO are as described in the examples.

FIG. 2 shows that the mRNA expression of the GABRB2 receptor is particularly increased compared to the control diet, when HMOs are administered in combination with BMO.

It should be recognized that the one or more examples in the disclosure are non-limiting examples and that the present disclosure is intended to encompass variations and equivalents of these examples.

The invention claimed is:

1. A method for improving, enhancing, promoting or modulating a) a GABAergic function in the central nervous system (CNS) or b) filtering of information or the capacity to focus or concentrate on a mental or physical activity in a mammal suffering from a health status or disease related to GABAergic function, the method comprising:
    administering a nutritional composition comprising an effective amount of a combination of a bovine milk oligosaccharide (BMO) and a human milk oligosaccharide (HMO) to the mammal suffering from the health status or disease related to GABAergic function, wherein the HMO comprises a combination of 2'fucosyllactose (2FL) and lacto-N-neotetraose (LNnT).

2. The method according to claim 1, wherein the GABAergic function in the CNS comprises filtering of information or a capacity to focus or concentrate on a mental or physical activity.

3. The method according to claim 1, wherein the HMO is present in an amount of from 0.01 to 50 g/L of the nutritional composition.

4. The method according to claim 1, wherein the nutritional composition further comprises a prebiotic.

5. The method according to claim 1, wherein the mammal is selected from the group consisting of a human, a pet, a cat and a dog.

6. The method according to claim 1, wherein the nutritional composition is selected from the group consisting of an infant formula, a follow on formula, a human milk fortifier, a growing up milk, and a pet food or supplement.

7. A method for treating at least one condition selected from the group consisting of attention deficit disorders, hyperactivity disorders, autism spectrum disorders, and schizophrenia in a mammal having the at least one condition, the method comprising:
  administering a nutritional composition comprising an effective amount of a combination of a bovine milk oligosaccharide (BMO) and a human milk oligosaccharide (HMO) to the mammal having the at least one condition,
  wherein the HMO comprises a combination of 2'fucosyl-lactose (2FL) and lacto-N-neotetraose (LNnT).

8. The method according to claim 7, wherein the HMO is present in an amount from 0.01 to 50 g/L of the nutritional composition.

9. The method according to claim 7, wherein the nutritional composition comprises a prebiotic.

10. The method according to claim 7, wherein the mammal is selected from the group consisting of a human, a pet, a cat and a dog.

11. The method according to claim 7, wherein the nutritional composition is selected from the group consisting of an infant formula, a follow on formula, a human milk fortifier, a growing up milk, and a pet food or supplement.

* * * * *